United States Patent
Singleton et al.

(10) Patent No.: US 6,384,023 B2
(45) Date of Patent: May 7, 2002

(54) SILICONE GEL CONTAINING SALICYLIC ACID

(75) Inventors: Laura C. Singleton, Los Angeles; Carol J. Collins, Granada Hills; Frederick W. Woodin, Jr., Pacific Palisades, all of CA (US)

(73) Assignee: Neutrogena Corporation, Los Angeles, CA (US)

( * ) Notice: Subject to any disclaimer, the term of this patent is extended or adjusted under 35 U.S.C. 154(b) by 0 days.

(21) Appl. No.: 09/800,356

(22) Filed: Mar. 6, 2001

Related U.S. Application Data

(63) Continuation of application No. 09/322,525, filed on May 28, 1999, now Pat. No. 6,200,964.

(51) Int. Cl.$^7$ ............................................. A61K 31/60
(52) U.S. Cl. ........................................................ 514/159
(58) Field of Search .......................................... 514/159

(56) References Cited

U.S. PATENT DOCUMENTS

| | | | |
|---|---|---|---|
| 4,212,759 A | 7/1980 | Young et al. | |
| 4,268,499 A | 5/1981 | Kell | |
| 4,514,385 A | 4/1985 | Damani et al. | |
| 5,143,722 A | 9/1992 | Hollenberg et al. | |
| 5,162,378 A | 11/1992 | Guthauser | |
| 5,296,476 A | 3/1994 | Henderson | |
| 5,549,888 A | 8/1996 | Venkateswaran | |
| 5,563,197 A | 10/1996 | Donatelli et al. | |
| 5,599,533 A | 2/1997 | Stepniewski et al. | |
| 5,623,017 A | 4/1997 | Hill | |
| 5,654,362 A | 8/1997 | Schulz, Jr. et al. | |
| 5,707,635 A | 1/1998 | Deckner et al. | |
| 5,750,123 A | 5/1998 | Znaiden et al. | |
| 5,833,998 A | 11/1998 | Biedermann et al. | |
| 5,834,513 A | 11/1998 | Ptchelintsev et al. | |
| 5,853,741 A | 12/1998 | Znaiden et al. | |
| 5,891,470 A | 4/1999 | Rinaldi et al. | |
| 5,919,437 A | 7/1999 | Lee et al. | |
| 5,929,164 A | 7/1999 | Zhang | |
| 5,932,229 A | * 8/1999 | Ptchelintsev et al. | |
| 5,980,921 A | 11/1999 | Bledemann et al. | |
| 6,017,552 A | 1/2000 | Mori | |
| 6,146,664 A | * 11/2000 | Siddiqui | |
| 6,183,766 B1 | * 2/2001 | Sine et al. | |

FOREIGN PATENT DOCUMENTS

| | | |
|---|---|---|
| EP | 0 359 475 A2 | 9/1989 |
| EP | 0 827 983 A2 | 3/1998 |
| WO | WO 99/24011 | 5/1999 |

OTHER PUBLICATIONS

PCT Search Report dated Oct. 16, 2000 for international application No. PCT/US 00/13809.

H.D. Goulden, Emil G. Klamann, Donald H. Powers, Cosmetics Science and Technology, (1957) Interscience Publishers, Inc., New York, 189–212.

* cited by examiner

*Primary Examiner*—William R. A. Jarvis
*Assistant Examiner*—Vickie Kim
(74) *Attorney, Agent, or Firm*—William E. McGowan

(57) ABSTRACT

The present invention relates to a silicone gel comprising a volatile liquid, a silicone polymer, and salicylic acid; compositions comprising the silicone gel; and methods of using such gel and composition for the prevention and treatment of acne or seborrhea.

26 Claims, No Drawings

SILICONE GEL CONTAINING SALICYLIC ACID

RELATED APPLICATIONS

This application is a continuation of U.S. patent application Ser. No. 09/322,525 filed May 28, 1999, now U.S. Pat. No. 6,200,964.

BACKGROUND OF THE INVENTION

Acne is a condition of the human skin characterized by the excess flow of sebum from sebaceous glands. Excess sebum (e.g., skin oil) on the person's skin inhibits the flow of sebum from hair follicles, causing it to thicken and form a solid plug within the follicle known as a comedone. The formation of comedones stimulates hyperkeratinization, resulting in a closing of the follicle opening. The closed follicle usually results in either a papule, a pustule, or a cyst that becomes infected with bacteria such a p-acnes. This infection is known as acne, or in lesser severity, seborrhea.

Salicylic acid is a known keratolytic agent that has the ability to both penetrate and dissolved comedones as well as kill bacteria (e.g., p. acnes). Salicylic acid, however, has very limited solubility in water and, thus, has typically been formulated in oil-in-water pigmented cosmetic formulations. The use of the oil-in-water formulations, however, does not assist in the absorption of oil from the skin but, rather, just adds more oil to the person's skin.

The present invention relates a topical silicone gel or a topical composition containing the gel (e.g., a water-in-silicone cosmetic foundation). The gel comprises salicylic acid for the treatment of acne and seborrhea. The gel also provides the additional benefit of oil absorbing properties. The oil absorbing properties both assist in the treatment of acne and seborrhea by absorbing excess sebum. In addition, the gel produces a desirable smooth matte finish on the skin treatment area.

SUMMARY OF THE INVENTION

In one aspect, the invention features a silicone gel comprising a volatile liquid, a silicone polymer, and salicylic acid. In one embodiment, the silicone polymer is polysilicone-11. In one embodiment, the volatile liquid is a silicone fluid (e.g., cyclomethicone). In one embodiment, the silicone gel further comprises a second liquid (e.g., dimethicone or a solvent of oalicylic acid). In one embodiment, the solvent is a non-alcohol solvent such as ester, e.g., neopentyl glycol dioctanoate/diisostearate, octyl salicylate, and octyl methoxycinnamate). In one embodiment, the silicone gel further comprises a porous silica (e.g., having a pore volume of 0.1 to about 1 ml/g, a particle diameter of between 1–20 microns, and/or an oil absorbence of between 10–500 ml/100 g). In one embodiment, the gel further comprises petrolatum. In one embodiment, the gel further comprises additional dermatologically active agents such as the anti-acne agents (e.g., benzoyl peroxide, resorcinol, sulfur, sodium borate, thymol, a retinoid, zinc sulfide, or zinc oxide), α-, β-, and polyhydroxy acids (e.g., lactic, glycolic, malic, tartaric, and citric acids) and/or anti-microbial or anti-inflammatory agents (e.g., alpha-bisabolol).

In one embodiment, the silicone gel comprises by weight: (a) about 1% to about 99% (e.g., about 10% to about 80%) of the volatile liquid (e.g., cyclomethicone); (b) about 1% to about 90% (e.g., about 10% to about 50%) of the silicone polymer (e.g., polysilicone-11); and (c) about 0.001% to about 50% (e.g., about 1% and about 30%) of the salicylic acid. In a further embodiment, the silicone gel further comprises by weight: (d) about 0.001% to about 50% (e.g., about 0.001% to about 30%) of dimethicone; (e) about 0.001% to about 50% (e.g., about 0.001% to about 30%) of neopentyl glycol dioctanoate/diisostearate; (f) about 0.001% to about 50% (e.g., about 0.001% to about 30%) of porous silica; and/or (g) about 0.001% to about 20% (e.g., about 0.001% to about 5%) of alpha-bisabolol.

In another aspect, the present invention features a composition comprising: (a) the above described silicone gel; and (b) a cosmetically acceptable carrier. In one embodiment, the cosmetically acceptable carrier comprises one or more of the members selected from the group consisting of acidifying agents, alkalizing agents, aerosol propellants, antimicrobial agents, antioxidants, buffering agents, chelating agents, coloring additives, dermotologically active agents, dispersing agents, emollients, emulsifying agents, humectants, fragrances, preservatives, sugars, sunscreen agents, surfactants, suspending agents, thickening agents, and vehicles.

In one embodiment, the composition is a water-in-silicone emulsion comprising by weight: (a) about 0.001% to about 90% (e.g., about 1% to about 50%) of the silicone gel; (b) about 0.001% to about 50% (e.g., about 5% to about 50%) of liquid silicone (e.g., cyclomethicone, dimethicone, or mixtures thereof); and (c) water, e.g., q.s. to 100%, by weight, once all the other ingredients have been added. In a further embodiment, the composition further comprises by weight: (d) about 0.001% to about 50% (e.g., about 0.001% to about 20%) of a humectant (e.g., dipropylene glycol); and (e) about 0.001% to about 50% (e.g., about 0.001% to about 20%) of sunscreen (e.g., titanium dioxide).

In another aspect, the present invention features method of treating (e.g., reducing or eliminating) or preventing acne and seborrhea (e.g., on the skin of a human), the method comprising applying to the skin of a subject an effective amount of the above mentioned silicone gel or composition. In one embodiment, the gel or composition is applied to the skin one to three times daily. When used in treating acne, the composition may be applied until the acne has been successfully treated (e.g., eliminated). When used as a prophylactic for acne, the composition may be applied daily until the risk of acne has subsided. The gel and composition may also be used to treat wrinkles, psoriasis, and hyperpigmentation, smooth skin, reduce skin lines, improve skin clarity and tone, and treat dandruff and seborrheic dermatitis (e.g., in a scalp cream, shampoo, or hair conditioner).

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to a novel silicone gel that both delivers salicylic acid while simultaneously possessing oil-absorbing properties. The present invention also features a cosmetic composition containing the gel (e.g., the gel is dispersed throughout the composition). The silicone gel is made, in one embodiment, by dispersing oil swellable silicone polymer (e.g., polysilicone-11) in a volatile liquid (e.g., silicone fluid such as cyclomethicone) or a volatile liquid mixed with other ingredients (e.g., dimethicone). Salicylic acid is then dispersed in the silicone gel, e.g., by either (i) adding salicylic acid powder to the silicone gel and milling the mixture to ensure homogeneous distribution of the salicylic acid in the gel or (ii) dissolving the salicylic acid in a solvent (e.g., an ester such as neopentyl glycol dioctanoate/diisostearate) and then uniformly dispersing the salicylic acid solution in the silicone gel. Salicylic acid is available from a number of commercial sources such as Spectrum Chemical, Gardena, Calif.

Upon spreading on skin (e.g., facial skin), the silicone gel releases the volatile liquid, delivers salicylic acid to the skin, and absorbs non-volatile excess skin oil present on the skin (e.g., the oil is absorbed by the oil-swellable silicone polymer and, if present, porous silica). The composition's ability to absorb sebum helps the skin maintain an environment that is less conducive to clogged pores, thereby, inhibiting the formation of comedones. The silicone gel may also contain porous silica that further enhances the oil-absorbing properties of the gel. The gel additionally has the ability to scatter incoming rays of light in all directions. By diminishing reflected light, the skin, thus, has a smooth matte appearance.

As used herein, the term "volatile" refers to those liquids that have a measurable vapor pressure at ambient temperature. Examples of volatile liquids include branched or straight chained hydrocarbons (e.g., C3–C20 hydrocarbons such as isoparaffins, isoeicosane, isohexadecane and isododecane) and silicone fluids. Examples of volatile silicone fluids include the following: cyclic and linear polydimethylsiloxanes containing from about 3 to about 9 (e.g., from about 4 to about 5) silicone atoms such as cyclomethicones; Dow Corning 200, Dow Coring 344, and Dow Corning 345 (manufactured by Dow Corning, Midland, Mich.); Silicone 7158 and 7207 (manufactured by Union Carbide, Houston, Tex.); SF 1202 (manufactured by General Electric); and SWS-03314 (manufactured by SWS Silicones, Inc.). As used herein, the term cyclomethicone refers to cyclotrisiloxane, cyclotetrasiloxane, cyclopentasiloxane, cyclohexasilxane, or mixtures thereof.

The silicone polymers of the present invention may have an average molecular weight in excess of 10,000 (e.g., between about 10,000 and 10,000,000). Examples of silicone polymers include crosslinked siloxane (e.g., dimethicone or dimethicone derivatives) copolymers such as stearyl methyl-dimethyl siloxane copolymer (Gransil SR-CYC, available from Grant Industries, Elmwood Park, N.J.); Polysilicone-11 (i.e., a crosslinked silicone rubber formed by the reaction of vinyl terminated silicone and methylhydrodimethyl siloxane in the presence of cyclomethicone), cetearyl dimethicone/vinyl dimethicone crosspolymer (i.e., a copolymer of cetearyl dimethicone crosslinked wit vinyl dimethyl polysiloxane), dimethicone/phenyl vinyl dimethicone crosspolymer (i.e., copolymer of dimethylpolysiloxane crosslinked with phenyl vinyl dimethylsiloxane), and dimethicone/vinyl dimethicone crosspolymer (i.e., copolymer of dimethylpolysiloxane crosslinked with vinyl dimethylsiloxane).

The silicone gels may also be purchased from commercial suppliers such as Grant Industries. Examples of such gels include cyclomethicone (and) polysilicone-11 (Gransil GCM5), cyclotetrasiloxane(D4) (and) petrolatum (and) polysilicone-11 (Grangil PS-4), cyclopentasiloxane(D5) (and) petrolatum (and) polysilicone-11 (Gransil PS-5), cyclopentasiloxane(D5) (and) dimethicone (and) polysilicone-11 (Gransil DMCM-5), cyclotetrasiloxane(D4) (and) dimethicone (and) polysilicone-11 (Gransil DMCM-4), polysilicone-11 (and) isododecane (Gransil IDS), and cyclomethicone (and) polysilicone-11 (and) petrolatum (and) phytosphingosine (Gransil SPH). Examples of such gels available from General Electric include cyclopentasiloxane (and) dimethicone/vinyl dimethicone crossploymer (SFE839).

The invention features a cosmetic composition for application to the skin, e.g., the face, of a subject comprising a cosmetically acceptable carrier. The individual components of the carrier are numerous and varied, but are also well known to one skilled in the art. In one aspect, the carrier comprises one or more of the members selected from the group consisting of acidifying agents, alkalizing agents, aerosol propellants, antimicrobial agents, antioxidants, buffering agents, chelating agents, coloring additives, dermotologically active agents, dispersing agents, emollients, emulsifying agents, fragrances, humectants, masking agents, preservatives, sugars, sunscreen agents, surfactants, suspending agents, thickening agents, an vehicles. These ingredients are discussed below. Examples of these agents are listed below as well as in the International Cosmetic Ingredient Dictionary and Handbook, eds. Wenninger and McEwen (The Cosmetic, Toiletry, and Fragrance Assoc., Washington, D.C., $7^{th}$ Edition, 1997) (hereinafter "ICT Handbook").

Acidifying and alkalizing agents are added to obtain the desired pH of the composition. Examples of acidifying agents included acetic acid, citric acid, glacial acetic acid, malic acid, and proprionic acid. Examples of alkalizing agent include edetol, potassium carbonate, potassium hydroxide, sodium borate, sodium carbonate, and sodium hydroxide. Other acidifying and alkalizing agents are listed on page 1653 of the ICT Handbook.

Aerosol propellants are used when the composition is to be administered as an aerosol under pressure. Examples of aerosol propellants include halogenated hydrocarbons such as dichlorodifluoromethane, dichlorotetrafluoroethane, and trichloromonofluoromethane, nitrogen, and volatile hydrocarbons such as butane, propane, isobutane, or mixtures thereof. Other propellants are listed on page 1655 of the ICT Handbook.

Anti-microbial agents are used when the area that the composition is to be applied is prone to microbial infection, e.g., by bacteria, fungal, or protozoa. Examples of such agents include benzyl alcohol, chlorobutanol, phenylethyl alcohol, phenylmercuric acetate, potassium sorbate, and sorbic acid, benzoic acid, butyl paraben, ethyl paraben, methyl paraben, propyl pareben, and sodium benzoate. Other anti-microbial agents are listed on page 1612 of the ICT Handbook.

Antioxidants are used to protect ingredients of the composition from oxidizing agents that are included within or come in contact with the composition. Examples of antioxidants include water.soluble antioxidants such as ascorbic acid, sodium sulfite, metabisulfite, sodium miosulfite, sodium formaldehyde, sulfoxylate, isoascorbic acid, isoascorbic acid, cysteine hydrochloride, 1,4-diazobicyclo-(2,2,2)-octane, and mixtures thereof. Examples of oil-soluble antioxidants include ascorbyl palmitate, butytlated hydroxyanisole, butylated hydroxytoluene, potassium propyl gallate, octyl gallate, dodecyl gallate, phenyl-α-napthylamine, and tocopherols such as α-tocopherol. Other antioxidants are listed on pages 1612–13 of the ICT Handbook.

Buffering agents are used to maintain an established pH of the composition. Examples of buffering agents included sodium citrate, calcium acetate, potassium metaphosphate, potassium phosphate monobasic, and tartaric acid. Other buffering agents are listed on page 1653 of the ICT Handbook.

Chelating agents are used to maintain the ionic strength of the composition and/or bind to destructive compounds and metals that are included within or come in contact with the composition. Examples of chelating agents included dihydroxy ethyl glycine, citric acid, tartaric acid, edatate dipotassium, edetate disodium, edetic acid, and ethylenediamine tetracetic acid (EDTA) and its salts (e.g., tetrasodium EDTA). Other chelating agents are listed on page 1626 of the ICT Handbook.

Coloring additives are used to add color to the composition. Examples of such coloring additives include titanium dioxide, yellow iron oxide, red iron oxide, black iron oxide, caramel, carmine, fluorescein derivatives, methoxsalen, trioxsalen, carbon black, azo dyes, anthraquinone dyes, blue azulenes, guajazulene, chamuzulene, erythrosin, bengal rose, phloxin, cyanosin, daphinin, eosin G, cosin 10B, and Acid Red 51. Other coloring agents are listed on pages 1628–30 of the ICT Handbook.

Dermatologically active agents include agents for treating wound healing, inflammation, acne, psoriasis, cutaneous aging, skin cancer, impetigo, herpes, chickenpox, dermatitis, pain, itching, and skin irritation. Examples of such dermatologically active agents include hydrocortisone, dexamethesone, panthenol, phenol, tetracycline hydrochloride, yeast, hexylresorcinol, lamin, kinetin, betamethagone, triamcinolone, fluocinolone, methylprednisolone, retinoids such as retinol and retinoic acid, dapsone, sulfasalazine, resorcinol, salicylic acid, benzoyl peroxide, erythromycin-benzoyl peroxide, erythromycin, clindamycin, mupirocin, griseofulvin, azoles such as miconazole, econazole, itraconazole, fluconazole, and ketoconazole, ciclopirox, allylamines such as naftifine and terfinafine, acyclovir, famciclovir, valacyclovir, benzocaine, lidocaine, dibucaine, pramoxine hydrochloride, methyl salicylate, camphor, menthol, resocinol, and vitamins such as tocopherol, tocopheryl acetate, pentothenic acid, ascorbic acid, biotin, and retinoids such as retinol, retinoic acid, retinal, retinyl acetate, and retinyl palmitate, α-hydroxy acid, a β-hydroxy acid, or poly-hydroxy acid such as glycolic acid, lactic acid, citric acid, malic acid, and azaleic acid, and sunless tanning agents such as 1,3-dihydroxyacetone and 1,3,4-trihydroxy-2-butanone (erythulose).

Examples of dispersing and suspending agents include quarternium-18 hectorite, polyhydroxy stearic acid, poligeenan and silicon dioxide. Other dispersing and suspending agents are listed on page 1690–91 of the ICT Handbook.

Emollients are agents that soften and smooth the skin. Examples of emollients include hydrocarbon oils and waxes (e.g., natural and synthetic waxes) such as mineral oil, petrolatum, microcrystaline wax, polyethylene, triglyceride esters such as those of castor oil, cocoa butter, safflower oil, cottonseed oil, corn oil, olive oil, cod liver oil, almond oil, avocado oil, palm oil, sesame oil, squalene, and soybean oil, acetylated monoglycerides, ethoxylated glycerides, fatty acids, alkyl esters of fatty acids, alkenyl esters of fatty acids, fatty alcohols, fatty alcohol ethers, ether-esters, lanolin and derivatives of lanolin, polyhydric alcohol esters, wax esters such as beeswax, vegetable waxes, phospholidds, and sterols. Other emollients are listed on pages 1656–61 of the ICT Handbook.

Emulsifying agents are used for preparing emulsions of the present invention. Examples of emulsifying agents used for preparing water-in-oil emulsions include cyclomethicone (and) dimethicone copolyol, dimethicone copolyol, cetyl dimethicone copolyol, PEG-30 dipolyhydroxystearate, and PEG-40 sorbitan peroleate. Examples of emulsifying agents used for preparing oil-in-water emulsions of the present invention include glyceryl stearate, PEG-100 stearate, methyl gluceth sesquisterate, fatty alcohols, and alkyl phenols condensed with ethylene oxide. Other emulsifiers are listed on pages 1679–87 of the ICT Handbook. Emulsion stabilizers are listed on pages 1634–35 of the ICT Handbook.

Humectants are agents that promote the retention of moisture, e.g., moisturizers. Examples of humectants include sorbitol, matricaria extract, aloe barbadensis gel, glycerin, glycereth 5 lactate, glycereth 7 triacetate, glycereth 7 diisononoate, hexanetriol, hexylene glycol, propylene glycol, dipropylene glycol, alkoxylated glucose, D-panthenol, 1-2-pantandiol, 2-methyl-1,3-propanediol, and derivatives thereof, and hyaluronic acid. Other humectants are listed on pages 1661–62 of the ICT Handbook.

Examples of fragrances include peppermint, rose oil, rose water, aloe vera, clove oil, menthol, camphor, eucalyptus oil, and other plant extracts. Certain fragrances may require a solubilizer, e.g., PPG-5-ceteareth-20. To eliminate certain odors from compositions, masking agents may be used. An example of a masking agent includes ethylene brassylate. Other fragrances and masking agents are listed on pages 1639–40 of the ICT Handbook.

Preservatives are used to protect the composition from degradation. Examples of preservatives include liquipar oil, phenoxyethanol, methyl paraben, propyl paraben, butyl paraben, isopropyl paraben, isobutyl paraben, dieizolidinyl urea, imidazolidinyl urea, diazolindyl urea, benzalkonium chloride, benzethonium chloride, phenol, and mixtures thereof (e.g., liquipar oil). Other preservatives are listed on pages 1654–55 of the ICT Handbook.

Examples of sugars include monosaccharides, disaccharides, and polysccharides such as glucose, xylose, fructose, reose, ribose, pentose, arabinose, allose, tallose, altrose, mannose, galactose, lactose, sucrose, erythrose, glyceraldehyde, or any combination thereof.

Sunscreen agents are agents used to block or reduce the amount of ultraviolet radiation impinging on the skin (e.g., by absorption, scattering, and reflection of the ultraviolet radiation). Segarin, et al., Cosmetics Science and Technology, Chapter VIII, pages 189, et seq. discloses numerous examples of sunscreen agents. Examples of sunscreen agents include both organic compounds and their salts such as octyl methoxycinnamate, octyl salicylate, benzophenone-3 homosalate, octocrylate, avobenzone, and menthyl anthranilate, as well as inorganic particulate materials such as zinc oxide, silica, iron oxide, titanium dioxide, and 2-ethyl-hexyl-p-methoxycinnamate. Other sunscreen agents are listed on page 1672 of the ICT Handbook. Generally, the composition will contain from about 1% to about 30%, by weight, of sunscreen agent(s). The exact amounts will vary depending on the sunscreen used and the desired sun-protection factor (SPF).

Surfactants are agents used to stabilize multi-component compositions, e.g., used as wetting agents, antifoam agents, emulsifiers, dispersing agents, and penetrants. Examples of surfactants include methyl gluceth 20, decyl polyglucoside, lapyrium chloride, laureth 4, laureth 9, monoethanolamine, nonoxynol 4, nonoxynol 9, nonoxynol 10, nonoxynol 15, nonoxynol 30, poloxalene, polyoxyl 8, 40, and 50 stearate, polysorbate 20, polysorbate 40, polysorbate 60, polysorbate 65, polysorbate 80, and polysorbate 85, sodium lauryl sulfate, sorbitan and its derivatives. Other surfactants are listed on page 1672–90 of the ICT Handbook.

Vehicles are often referred to as the base for the cosmetically acceptable carrier, e.g., a fluid that is capable of delivering the other components of the composition to the skin with acceptable absorption of those components into the skin. Examples of vehicles include water, e.g., deionized water, saline (e.g., sodium chloride dissolved in deionized water), oil-in-water emulsions (e.g., where the Continuous water phase contains the water soluble agents and the discontinuous oil phase contains the oil soluble agents), and water-in-oil emulsions (e.g., where the continuous oil phase contains the oil soluble agents and the discontinuous water phase contains the water soluble agents). The oil phase may be established by the addition of hydrocarbon and/or silicone fluids, e.g., cyclomethicone and dimethicone, together with various suitable emulsifying agents. In order to reduce applying additional oil to the skin of the subject, hydrocarbon oils should be avoided.

The cosmetically acceptable Carrier that may be in a number of different delivery forms, e.g., a spray, mist, aerosol, shampoo, hair conditioner, mousse, semi-solid cream, liquid such as a solution, emulsion, or suspension, lotion, gel, solid such as a powder, adherent stick, flexible mask, self-hardening liquid or gel, or other suitable forms intended to be applied to the skin of a subject (e.g., a human). Water-in-oil emulsions (e.g., ratio of about 2:1 to about 1:100 such as about 1:1 to about 1:10) and oil-in-water emulsions (e.g., ratio of about 2:1 to about 1:100 such as about 1:1 to about 1:10) are typically used in preparing lotions and creams. The actual ratio of the two phases will depend on the consistency of the desired final product.

The viscosity of the compositions of the present invention may be different dependent upon the type of formulation being prepared, e.g., a liquid formulation will have a lower viscosity than a gel or cream formulation. Typically, the viscosity of liquid formulations of the present invention will range from 5,000 to 25,000 cps. Bulking agents may be used to increase the viscosity of the composition. An example of a bulking agent is talc. Other bulking agents are listed on page 1625–26 of the ICT Handbook. Other viscosity increasing agents are listed on pages 1693–97 of the ICT Handbook. Viscosity decreasing agents are listed on pages 1692–92 of the ICT Handbook.

The compositions of the present invention may be prepared using methodology that is well known by an artisan of ordinary skill (e.g., by using well-known mixing and blending procedures). For examples, for emulsion compositions of the present invention, each phase of the emulsion may be separately prepared with all of the components contained in their appropriate phases. The emulsion is then formed by adding one phase to the other phase with agitation.

The gel or compositions of the present invention may be packaged in a container that is well known by an artisan of ordinary skill, e.g., the silicone gel may be packaged in a low density polyethylene tube with a dispensing tip head and the cosmetic foundation of the present invention may be packaged in a glass or plastic bottle.

The following is a description of the manufacture of specific gels and compositions of the present invention.

Other gels and compositions of the invention can be prepared in an analogous manner by a person of ordinary skill in the art.

EXAMPLE 1

Topical Silicone Gel

The ingredients and their respective weight percentages with respect to the total composition for the cosmetic product of Example 1 are recited below in Table 1.

TABLE 1

| INGREDIENT | WEIGHT (%) |
|---|---|
| Cyclopentasiloxane(D5) (and) Dimethicone (and) Polysilicone-11 (30:30:40) | 85.81 |
| Neopentyl Glycol Dioactonate/Diisostearate | 5.50 |
| Salicylic Acid | 0.55 |
| Alpha-bisabolol | 0.10 |
| Fragrance | 0.04 |
| Porous Silica | 8.00 |
| | 100.00 |

The cyclopentasiloxane (D5) (and) dimethicone (and) polysilicone-11 gel (Gransil DMCM-5, Grant Industries) was added to a main beaker. The neopentyl glycol dioctnoate/diisosteaate (Minno 21, Bernel Co., Elmwood, N.J.) and the salicylic acid were then added to a second beaker, mixed, and heated to between 50°–60° C. until the salicylic acid completely dissolved in the ether. The solution was allowed to cool to room temperature. Alpha-bisabolol and the fragrance were then added to the solution in the second beaker and mixed until homogenous. The ingredients of the second beaker were then added to the main beaker and mixed until homogenous. Lastly, silica was slowly added to the main beaker while mixing until uniform. The resulting gel had a viscosity of between 200,00 and 400,000 cps.

EXAMPLE 2

Water-in-silicone Cosmetic Skin Foundation Containing Silicone Gel

The ingredients and their respective weight percentages with respect to the total composition for the cosmetic product of Example 2 are recited below in Table 2.

TABLE 2

| INGREDIENT | WEIGHT (%) |
|---|---|
| Phase A | |
| Deionized Water | 32.95 |
| Sodium Chloride | 0.50 |
| Matricaria Extract | 1.00 |
| Aloe Barbadensis Gel | 0.01 |
| Diazolindyl Urea | 0.20 |
| Phase B | |
| Dipropylene Glycol | 4.00 |
| Methyl paraben | 0.15 |
| Phase C | |
| Polyglyceryl-4 Oleate (and) PEG-8 Propylene Glycol Cocoate (80:20) | 2.00 |
| Cyclomethicone (and) Dimethicone Copolyol (90:10) | 13.00 |
| Propyl paraben | 0.20 |
| Cyclomethicone (and) Quarternium18 (and) Hectorite (and) Propylene Carbonate (35:60:5) | 1.50 |
| Ethylene Brassylate | 0.20 |
| Synthetic Wax | 1.20 |
| C12–15 Alkyl Benzoate (and) Titanium Dioxide | 8.00 |

TABLE 2-continued

| INGREDIENT | WEIGHT (%) |
|---|---|
| (and) Alumina (and) Polyhydroxystearic Acid (and) Silica (60:30:5:2.5:2.5) | |
| *Phase D* | |
| Cyclomethicone | 9.69 |
| *Phase E* | |
| Talc | 6.40 |
| Silica Silyate | 0.50 |
| Polymethyl Methacrylate (and) tocopheryl acetate (and) pantothenic acid (and) ascorbic acid (and) retinyl palmitate (90:7:1:1:1) | 0.10 |
| Titanium Dioxide | 7.71 |
| Yellow Iron Oxide | 0.49 |
| Red Iron Oxide | 0.15 |
| Black Iron Oxide | 0.05 |
| *Phase F* | |
| Cyclomethicone (and) Salicylic acid (and) Polysilicone-11 (87.5:5.5:7) | 10.00 |
| | 100.00 |

The suppliers of the above listed ingredients are the following: matricaria extract (Active Oraganics; Lewisville, Tex.), polyglyceryl-4 oleate (and) PEG-8 Propylene Cocoate (Henkel, Dusseldorf, Germany); cyclomethicone (and) dimethicone copolyol (Dow Corning, Midland, Mich.); cyclomethicone (and) quarternium-18 (and) hectorite (and) propylene carbonate (Rheox, Philadelphia, Pa.); synthetic wax (Presperse, Piscataway, N.J.); C12–15 alkyl benzoate (and) titanium dioxide (and) polyhydroxystearic acid (and) silica (Tioveil, Durham, England); polymethyl methacrylate (and) tocopheryl acetate (and) pantothenic acid (and) ascorbic acid (and) retinyl palmitate (Brooks Industries; South Plainfield, N.J.); iron oxides (U.S. Cosmetic Corporation, Dayville, Conn.); and Cyclomethicone (and) polysilicone-11 (Grancil GCM5; Grant Industries, Elmwood Park, N.J.). The Cyclomethicone (and) polysilicone-11 (and) salicylic acid is manufactured by adding solid salicylic acid powder to the silicone gel and milling the mixture to ensure homogeneous distribution of the salicylic acid in the silicone gel. The cyclomethicone used the silicone gel was cyclopentasiloxane, but other cyclomethicones may be used (e.g., cyclotetrasiloxane).

The Phase C ingredients were added, in the order listed, into a stainless steel jacketed oil-phase kettle equipped with variable speed propeller agitation. The agitation was begun at a temperature of 20–30° C. as soon as the propeller was covered sufficiently to mix the ingredients without splashing ("Phase C Mixture"). Cold water should be used in the jacket as necessary to remove any heat generated from mixing and milling.

A W750 Colloid Mill (Greerco/Chemineer, North Andover, Mass.) was connected to the oil-phase kettle containing the Phase C Mixture and was set up to recirculate. A drop-in homogenizer was also placed in the oil-phase kettle. The propeller mixer in the oil-phase kettle was adjusted to create a vortex in the Phase C Mixture, and the ingredients of Phase E were added. After all the pigments had been added, the propeller speed was reduced so that air was not whipped into the mixture. The homogenizer and the colloid mill were then turned on. The gap set of the mill was initially set at "40," but it was immediately closed to between "4"–"6" ("Phase CE Mixture").

50–80% of the cyclomethicone in Phase D was added to the Phase CE Mixture to adjust the viscosity of the slurry so that it was a suitable viscosity to colloid mill properly. The batch was homogenized and milled (e.g., for at least 2 hours) until the dispersion was free of color spots when checked between two glass slides ("Phase CED Mixture").

The Gransil CGM5-SA of Phase F was then added to the Phase CED Mixture. Milling was continued for 20 minutes to insure that the Gransil CGM %-SA was uniformly dispersed. The gap set of the mill was opened to 40, and the colloid mill was turned off. The colloid mill was used to transfer the mixture to the main kettle. All of the remaining cyclomethicone from Phase D was used to rinse the bottom of the oil-phase kettle and the mill and added to the main kettle. The mill was attached to the main kettle and set up to recirculate ("Phase CEDF Mixture").

The Phase A ingredients were added, in the order listed, into a stainless steel jacketed water-phase kettle equipped with variable speed propeller agitation. The agitation was begun as soon as the propeller was covered sufficiently to mix without splashing ("Phase A Mixture"). The Phase B dipropylene glycol was placed into a suitable vessel, and the methyl paraben of Phase B was added the vessel and mixed until completely dissolved ("Phase B Mixture"). The Phase B Mixture was added to the water-phase kettle, and the resulting mixture was mixed with medium propeller agitation for a minimum of ten minutes or until clear ("Phase AB Mixture").

The Phase AB Mixture in the oil-phase kettle was added to the Silicone/Color Phase in the main kettle, i.e., Phase CEDF Mixture, in the following manner. A pump was connected to the water-phase kettle. The flow rate of the pump was checked by measuring the weight and time it takes to fill a 5-gallon pail about ½–¾ full. The Phase AB Mixture addition rate should be between 2 and 4 kg per minute. The Phase AB Mixture was added at a rate so that water did not pool on the surface of the main kettle. If water began to pool on the surface, the transfer pump was shut off, and the pooled water was allowed to be incorporated before continuing. The sweep and propeller mixers were activated during the water phase addition. As the level of the batch rose, the speed of the mixers were adjusted to maintain good mixing without splashing.

After the water phase addition was complete, the colloid mill (gap open at "40") was run for 15 seconds to flush out the bottom of the tank. The propeller and sweep mixers were allowed to mix the batch for 15 minutes. Upon completion of matching the shade and color of the composition, the viscosity of the batch was set by using the colloid mill to impart high sheer on the mixture in a single pass as it was removed from the main kettle. The gap on the colloid mill was set between "4" and "6" and the main kettle was drained.

The resulting composition comprised 0.55% of salicylic acid and had a viscosity of 14,000 cps. Other shades of this foundation can be obtained by varying the ratios of the iron oxide colorants.

EXAMPLE 3
Skin Foundation Containing Silicone Gel

The ingredients and their respective weight percentages with respect to the total composition for the cosmetic product of Example 3 are recited below in Table 3. The composition was manufactured following the protocol set forth in Example 1 except that Example 2's Phase F silicone gel ingredient was replaced with the new silicone gel cyclomethicone (and) dimethicone (and) polysilicone-11 (Grancil DMCM5; Grant Industries, Elmwood Park, N.J.). The cyclomethicone (and) dimethicone (and) polysilicone-11 (and) salicylic acid is manufactured by adding salicylic acid powder to the silicone gel and milling the mixture to ensure homogeneous distribution of the salicylic acid in the silicone gel. The cyclomethicone used in the silicone gel was cyclopentasiloxane, but other cyclomethicones may be used (e.g., cyclotetrasiloxane).

TABLE 3

| INGREDIENT | WEIGHT (%) |
|---|---|
| Phase A | |
| Deionized Water | 31.50 |
| Sodium Chloride | 0.50 |
| Panthenol | 1.00 |
| Milibiose | 0.25 |
| Matricaria Extract | 1.00 |
| Aloe Barbadensis Gel | 0.01 |
| Diazolindyl Urea | 0.20 |
| Phase B | |
| Dipropylene Glycol | 4.00 |
| Methyl paraben | 0.15 |
| Phase C | |
| Tocopheryl Acetate | 0.01 |
| Retinyl Palmitate | 0.01 |
| Polyglyceryl-4 Oleate (and) PEG-8 Propylene Glycol Cocoate (80:20) | 2.00 |
| Cyclomethicone (and) Dimethicone Copolyol (90:10) | 13.00 |
| Propyl paraben | 0.20 |
| Cyclomethicone (and) Quarternium18 (and) Hectorite (and) Propylene Carbonate (35:60:5) | 1.50 |
| Ethylene Brassylate | 0.20 |
| Synthetic Wax | 1.20 |
| Cyclomethicone (and) Dimethicone (and) Salicylic acid (and) Polysilicone-11 (31.5:31.5:31.5:5.5) | 8.80 |
| Phase D | |
| Cyclomethicone | 10.89 |
| Phase E | |
| Talc | 6.00 |
| Silica Silyate | 0.50 |
| C12–15 Alkyl Benzoate (and) Titanium Dioxide (and) Alumina (and) Polyhydroxystearic Acid (and) Silica (60:30:5:2.5:2.5) | 8.00 |
| Polymethyl Methacrylate (and) tocopheryl acetate (and) pantothenic acid (and) ascorbic acid (and) retinyl palmitate (90:7:1:1:1) | 0.10 |
| Titanium Dioxide | 7.35 |
| Iron Oxides | 0.49 |
| | 100.00 |

The resulting composition comprised 0.55% of salicylic acid and had a viscosity of 12,000 cps.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A water-in-silicone emulsion comprising by weight:
   (a) about 0.001% to about 50% of a silicone gel;
   (b) about 0.001% to about 50% of a liquid silicone; and
   (c) water;
   wherein said silicone gel consists of a volatile liquid silicone, a solid silicone polymer, and salicylic acid.

2. An emulsion of claim 1, wherein said silicone gel consists of by weight:
   (a) about 1% to about 99% of a volatile liquid silicone;
   (b) about 1% to about 90% of a solid silicone polymer; and
   (c) about 0.001% to about 50% of salicylic acid.

3. An emulsion of claim 2, wherein said silicone gel consists of by weight:
   (a) about 1% to about 99% of cyclomethicone;
   (b) about 1% to about 90% of polysilicone-11; and
   (c) about 0.001% to about 30% of salicylic acid.

4. An emulsion of claim 1, wherein said liquid silicone is a member selected from the group consisting of cyclomethicone, dimethicone, and mixtures thereof.

5. An emulsion of claim 2, wherein said liquid silicone is a member selected from the group consisting of cyclomethicone, dimethicone, and mixtures thereof.

6. An emulsion of claim 3, wherein said liquid silicone is a member selected from the group consisting of cyclomethicone, dimethicone, and mixtures thereof.

7. An emulsion of claim 2, wherein said composition further comprises by weight:
   (d) about 0.001% to about 50% of a humecant; and
   (e) about 0.001% to about 50% of a sunscreen.

8. An emulsion of claim 3, wherein said composition further comprises by weight:
   (d) about 0.001% to about 50% of a humectant; and
   (e) about 0.001% to about 50% of a sunscreen.

9. An emulsion of claim 6, wherein said composition further comprises by weight:
   (d) about 0.001% to about 50% of a humectant; and
   (e) about 0.001% to about 50% of a suncreen.

10. An emulsion of claim 7, wherein said humectant is dipropylene glycol and said sunscreen is titanium dioxide.

11. An emulsion of claim 8, wherein said humecant is dipropylene glycol and said sunscreen is titanium dioxide.

12. An emulsion of claim 9, wherein said humectant is dipropylene glycol and said sunscreen is titanium dioxide.

13. A composition of claim 1, wherein said composition further comprises a pigment.

14. A composition of claim 3, wherein said composition further comprises a pigment.

15. A composition of claim 6, wherein said composition further comprises a pigment.

16. A composition of claim 13, wherein said pigment is an iron oxide.

17. A composition of claim 14, wherein said pigment is an iron oxide.

18. A composition of claim 15, wherein said pigment is an iron oxide.

19. An emulsion of claim 1, wherein the ratio between said water phase and said silicone phase is from about 1:1 to about 1:10.

20. An emulsion of claim 3, wherein the ratio between said water phase and said silicon phase is from about 1:1 to about 1:10.

21. An emulsion of claim 4, wherein the ratio between said water phase and said silicone phase is from about 1:1 to about 1:10.

22. An emulsion of claim 6, wherein the ratio between said water phase and said silicone phase is from about 1:1 to about 1:10.

23. An emulsion of claim 1, wherein the said emulsion comprises about 9%, by weight, of water.

24. An emulsion of claim 3, wherein the said emulsion comprises about 9%, by weight, of water.

25. An emulsion of claim 4, wherein the said emulsion comprises about 9%, by weight, of water.

26. An emulsion of claim 6, wherein the said emulsion comprises about 9%, by weight, or water.

* * * * *